US009642601B2

(12) United States Patent
Shin et al.

(10) Patent No.: US 9,642,601 B2
(45) Date of Patent: May 9, 2017

(54) ULTRASOUND SYSTEM AND METHOD FOR PROVIDING PANORAMIC IMAGE

(71) Applicant: SAMSUNG MEDISON CO., LTD., Gangwon-Do (KR)

(72) Inventors: Seong-chul Shin, Gangwon-do (KR); Jae-yoon Shim, Gangwon-do (KR)

(73) Assignee: SAMSUNG MEDISON CO., LTD., Hongcheon-gun, Gangwon-do (KR)

( * ) Notice: Subject to any disclaimer, the term of this patent is extended or adjusted under 35 U.S.C. 154(b) by 565 days.

(21) Appl. No.: 14/015,502

(22) Filed: Aug. 30, 2013

(65) Prior Publication Data

US 2014/0063182 A1    Mar. 6, 2014

(30) Foreign Application Priority Data

Aug. 31, 2012  (KR) .................. 10-2012-0096316

(51) Int. Cl.
  *A61B 8/00*  (2006.01)
  *A61B 8/08*  (2006.01)

(52) U.S. Cl.
  CPC .......... *A61B 8/5276* (2013.01); *A61B 8/463* (2013.01); *A61B 8/5246* (2013.01); *A61B 8/0891* (2013.01); *A61B 8/469* (2013.01)

(58) Field of Classification Search
  None
  See application file for complete search history.

(56) References Cited

U.S. PATENT DOCUMENTS

| 6,193,660 B1* | 2/2001 | Jackson ............... A61B 8/00 600/443 |
| 6,224,552 B1 | 5/2001 | Jago et al. |
| 2008/0188744 A1 | 8/2008 | Fan et al. |

(Continued)

FOREIGN PATENT DOCUMENTS

| KR | 10-2006-0050433 A | 5/2006 |
| KR | 10-2012-0044265 A | 5/2012 |

OTHER PUBLICATIONS

Korean Office Action, w/ English translation thereof, issued in Korean Patent Application No. KR 10-2012-0096316 dated Nov. 28, 2013.

(Continued)

*Primary Examiner* — Kevin McInnish
(74) *Attorney, Agent, or Firm* — McDermott Will & Emery LLP

(57) ABSTRACT

Provided are an ultrasound system and method that can provide improved storage efficiency of a storage unit by storing only some of a plurality of ultrasound images needed to produce a panoramic image in the storage unit. The ultrasound system includes: an ultrasound data acquisition unit for sequentially acquiring ultrasound data corresponding to a living body; a processor for producing a plurality of ultrasound images by using the ultrasound data, setting a region of interest (ROI) on each of the ultrasound images, performing motion estimation between the plurality of ultrasound images to estimate motion of the ROI, and extracting ultrasound images needed for forming a panoramic image from the ultrasound images based on the estimated motion; and a storage unit for storing the extracted ultrasound images.

14 Claims, 7 Drawing Sheets

(56) References Cited

U.S. PATENT DOCUMENTS

2011/0142319 A1* 6/2011 Lee .................... G01S 7/52063
382/131
2011/0144495 A1* 6/2011 Wilkening ........... A61B 8/0883
600/443

OTHER PUBLICATIONS

Korean Notice of Allowance issued in Korean Application No. 10-2012-0096316 dated Jun. 19, 2014, w/English translation.

* cited by examiner

ULTRASOUND SYSTEM AND METHOD FOR PROVIDING PANORAMIC IMAGE

RELATED APPLICATIONS

This application claims the benefit of Korean Patent Application No. 10-2012-0096316, filed on Aug. 31, 2012, in the Korean Intellectual Property Office, the disclosure of which is incorporated herein in its entirety by reference.

BACKGROUND

1. Field

One or more embodiments of the present invention relate to an ultrasound system, and more particularly, to an ultrasound system and method adapted to store only ultrasound images needed to produce a panoramic image in a storage unit.

2. Description of the Related Art

Due to its non-invasive and non-destructive nature, an ultrasound system has been widely used in the medical field that requires information about the inside of living bodies. The ultrasound system also plays a critical role in the medical profession since it can provide real-time, high-resolution images of tissue of a living body to a doctor without the need for a surgical procedure that directly incises the living body for observation.

The ultrasound system provides a panoramic image based on ultrasound images continuously acquired as an ultrasound probe moves along a surface of a living body. That is, the ultrasound system acquires continuous ultrasound images as the ultrasound probe moves along the surface of the living body and synthesizes the acquired continuous ultrasound images to generate a panoramic image.

SUMMARY

One or more embodiments of the present invention include an ultrasound imaging system and method that are capable of improving a storage efficiency of a storage unit by storing only some of a plurality of ultrasound images needed to produce a panoramic image in the storage unit.

Additional aspects will be set forth in part in the description which follows and, in part, will be apparent from the description, or may be learned by practice of the presented embodiments.

According to one or more embodiments of the present invention, an ultrasound system includes: an ultrasound data acquisition unit that sequentially acquires ultrasound data corresponding to a living body; a processor that produces a plurality of ultrasound images by using the ultrasound data, sets a region of interest (ROI) on each of the ultrasound images, performs motion estimation between the plurality of ultrasound images to estimate motion of the ROI, and extract ultrasound images needed for forming a panoramic image from the ultrasound images based on the estimated motion; and a storage unit that stores the extracted ultrasound images.

According to one or more embodiments of the present invention, a method of providing a panoramic image includes: sequentially acquiring ultrasound data corresponding to a living body; producing a plurality of ultrasound images by using the ultrasound data; setting a region of interest (ROI) on each of the ultrasound images, performing motion estimation between the plurality of ultrasound images to estimate motion of the ROI, and extracting ultrasound images needed for forming a panoramic image from the ultrasound images based on the estimated motion; and storing the extracted ultrasound images in a storage unit.

The ultrasound system and method for providing a panoramic image according to the embodiments of the present invention allow only some of a plurality of ultrasound images needed to produce a panoramic image to be stored in a storage unit, thereby improving storage efficiency of the storage unit. Furthermore, the panoramic image may be provided without limitations on the time taken to create the panoramic image, which are caused by limited storage capacity of the storage unit.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
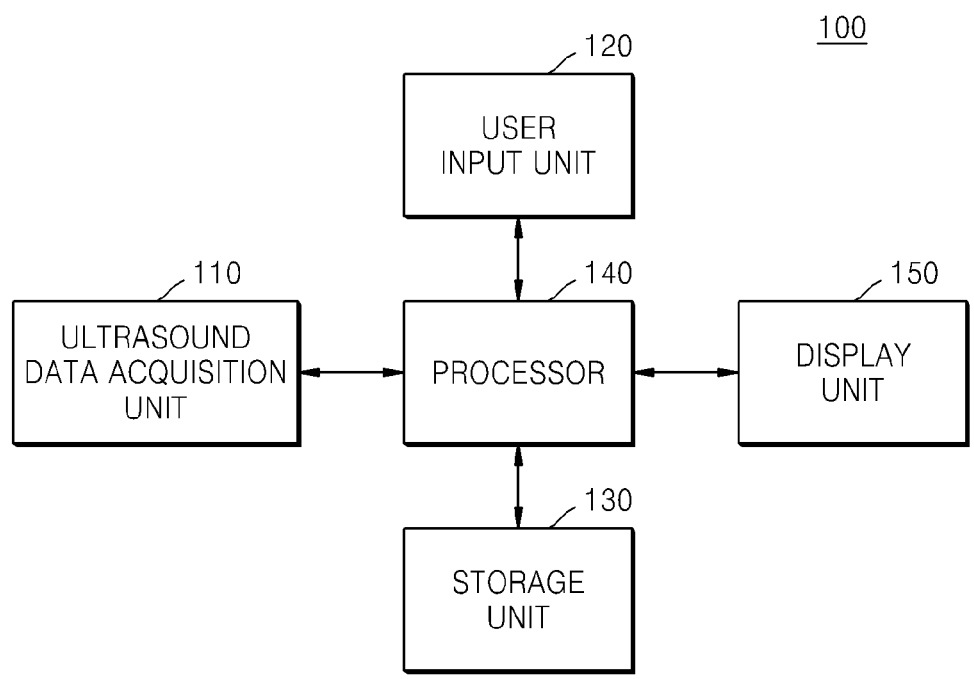
FIG. 1 is a block diagram showing a configuration of an ultrasound system according to an exemplary embodiment of the present invention.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

FIG. 1 is a block diagram illustrating a configuration of an ultrasound system 100 according to an exemplary embodiment of the present invention. Referring to FIG. 1, the ultrasound system 100 according to the present embodiment includes an ultrasound data acquisition unit 110.

The ultrasound data acquisition unit 110 transmits an ultrasound signal to a living body, including an object, such as blood vessels, the heart, and the bloodstream, and receives an ultrasound signal (i.e., ultrasound echo signal) reflected from the living body to acquire ultrasound data.

Figure 2:
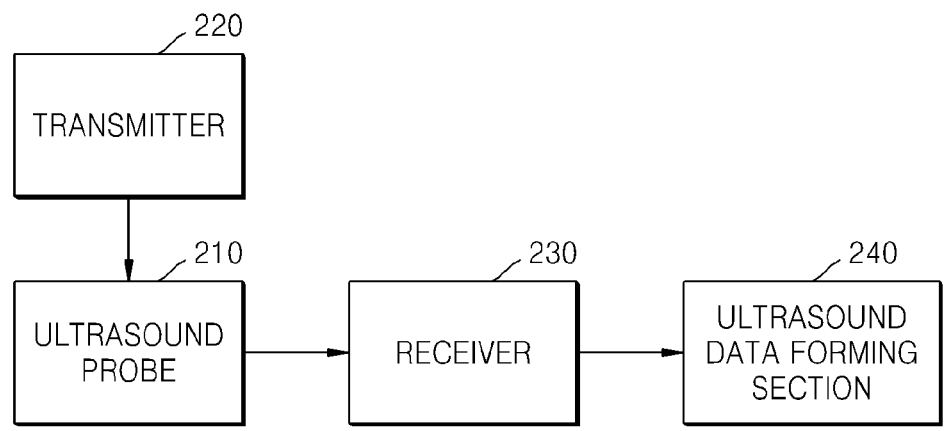
FIG. 2 is a block diagram showing a configuration of an ultrasound data acquisition unit in an ultrasound system, according to an exemplary embodiment of the present invention.

FIG. 2 is a block diagram showing a configuration of the ultrasound data acquisition unit 110 in the ultrasound system 100 of FIG. 1. Referring to FIG. 2, the ultrasound data acquisition unit 110 includes an ultrasound probe 210.

The ultrasound probe 210 includes a plurality of transducer elements (not shown) that convert electrical signals into ultrasound signals, and vice versa. The ultrasound probe 210 is configured to transmit an ultrasound signal to a living body and receive an ultrasound echo signal reflected from the living body to generate an electrical signal (hereinafter referred to as a "reception signal"). The reception signal is an analog signal. The ultrasound probe 210 includes a linear probe, but is not limited thereto.

The ultrasound data acquisition unit 110 further includes a transmitter 220 for controlling the transmission of an ultrasound signal. The transmitter 220 produces an electrical signal (hereinafter referred to as a "transmission signal") that is used to obtain an ultrasound image in consideration of transducer elements and a focal point. In the present embodiment, the transmitter 220 creates a transmission signal that is used to obtain each of a plurality of ultrasound images corresponding to a panoramic image. Thus, upon receipt of the transmission signal from the transmitter 220, the ultrasound probe 210 converts the transmission signal into an ultrasound signal, transmits the ultrasound signal to a living body, and creates a reception signal based on an ultrasound echo signal reflected from the living body.

The ultrasound data acquisition unit 110 further includes a receiver 230. The receiver 230 performs analog-to-digital conversion on the reception signal provided by the ultrasound probe 210 to produce a digital signal. The receiver 230 also performs reception beamforming on the digital signal in consideration of the transducer elements and a focal point to create a focused reception signal.

The ultrasound data acquisition unit 110 further includes an ultrasound data forming section 240. The ultrasound data forming section 240 creates ultrasound data corresponding to an ultrasound image by using the receive focused signal. According to the present embodiment, the ultrasound data forming section 240 forms ultrasound data corresponding to each of the ultrasound images by using the receive focused signal from the receiver 230. The ultrasound data includes radio frequency (RF) data, but is not limited thereto. the ultrasound data forming section 240 may also perform various signal processings, such as gain control needed to form ultrasound data, on the receive focused signal Referring back to FIG. 1, the ultrasound system 100 further includes a user input unit 120 for receiving user input information. The input information includes first input information needed for setting a region of interest (ROI) on an ultrasound image. The first input information contains information about the size and location (e.g., coordinates) of the ROI. The ROI will be described below in more detail. The input information also contains second input information. The user input unit 120 includes a control panel, a trackball, a mouse, and a keyboard.

Referring back to FIG. 1, the ultrasound system 100 further includes a storage unit 130. The storage unit 130 stores ultrasound data acquired by the ultrasound data acquisition unit 110 as well as ultrasound images needed to produce a panoramic image. In the present embodiment, the storage unit 120 includes a first storage section (not shown) for temporarily storing the ultrasound data acquired by the ultrasound data acquisition unit 110 and a second storage section (not shown) for storing the ultrasound images needed to produce a panoramic image.

The ultrasound system 100 further includes a processor 140. The processor 140 is connected to the ultrasound data acquisition unit 110, the user input unit 120, and the storage unit 130. The processor 140 includes a central processing unit (CPU), a microprocessor, and a graphic processing unit (GPU).

Figure 3:
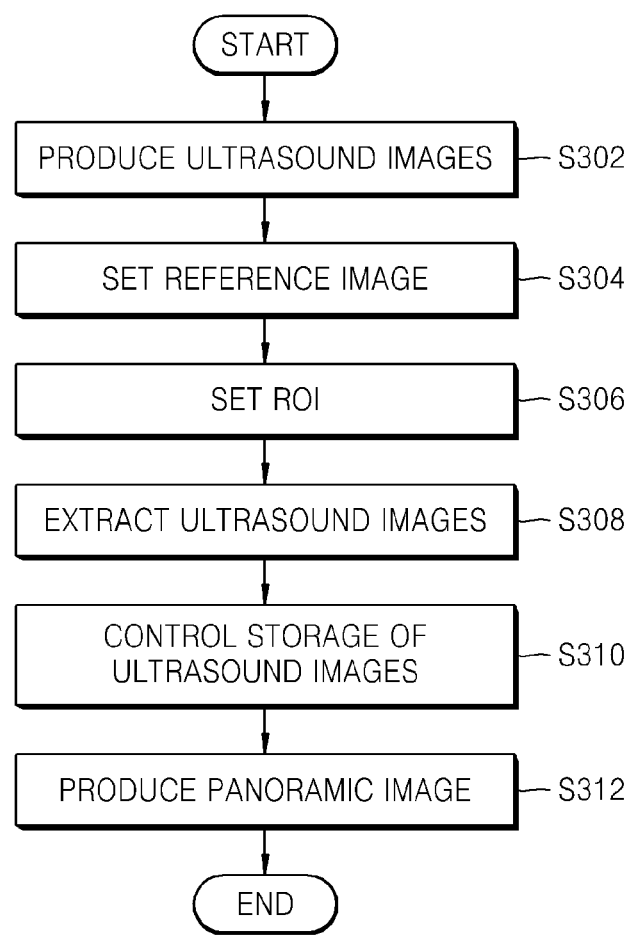
FIG. 3 is a flowchart of a method of producing a panoramic image, according to an exemplary embodiment of the present invention.
Figure 4:
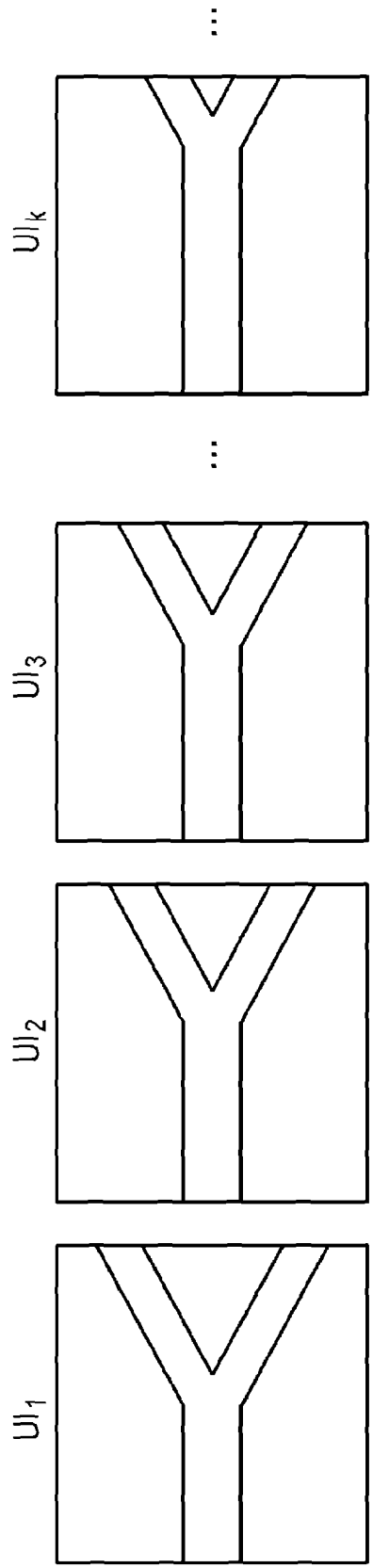
FIG. 4 illustrates a plurality of ultrasound images generated by an ultrasound system according to an exemplary embodiment of the present invention.

FIG. 3 is a flowchart of a method of producing a panoramic image, according to an exemplary embodiment of the present invention. Referring to FIGS. 1 and 3, the processor 140 produces ultrasound images by using ultrasound data provided by the ultrasound data acquisition unit 110 (S302). In the present embodiment, the processor 140 sequentially creates a plurality of ultrasound images UIi, as shown in FIG. 4, by using ultrasound data sequentially provided by the ultrasound data acquisition unit 110. In FIG. 4, i in UIi is an integer representing the order in which the ultrasound images are formed.

The processor 140 sets a reference image among the ultrasound images UIi (S304). In the present embodiment, the processor 140 sets a first ultrasound image UI1 as the reference image among the ultrasound images UIi. However, the present invention is not limited thereto. The reference image UI1 may be stored in the storage unit 130. The first ultrasound image UI1 may be displayed on a display unit 150. Thus, the user may set an ROI on the first ultrasound image UI1 displayed on the display unit 150 by using the user input unit 120.

Figure 5:
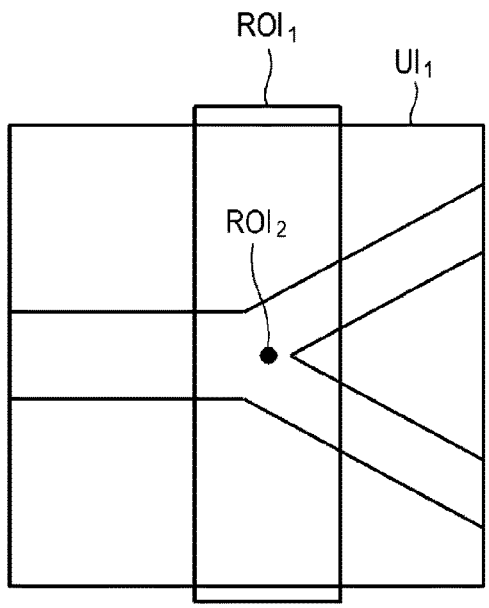
FIG. 5 is an exemplary diagram showing setting of a first region of interest (ROI) and a second ROI on a reference image, according to an exemplary embodiment of the present invention.

The processor 140 sets an ROI on the reference image UI1 based on input information (i.e., first input information) received from the user input unit 120 (S306). Referring to FIG. 5, the processor 140 sets a first ROI ROI1 and a second ROI ROI2 on the reference image UI1 based on the first input information needed for setting the first and second ROIs ROI1 and ROI2 as the ROI. The second ROI ROI2 may be set within the first ROI ROI1.

The processor 140 extracts ultrasound images needed to form a panoramic image from the ultrasound images UIi based on the input information, the reference image UI1, and the ROI (S308). The processor 140 controls the storage unit 130 to store the extracted ultrasound images therein (S310).

Figure 6:
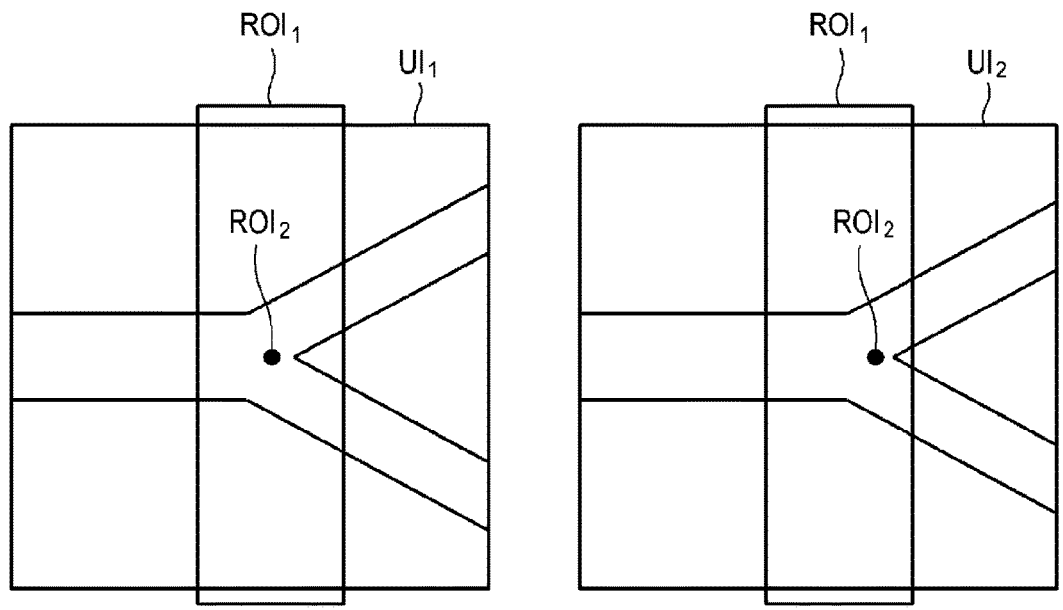
FIGS. 6 and 7 are exemplary diagrams showing setting of first and second ROIs on an ultrasound image, according to an exemplary embodiment of the present invention.

More specifically, referring to FIG. 6, in one embodiment, the processor 140 sets the first ROI ROI1 on the second ultrasound image UI2 based on input information (i.e., the first input information). In this case, the first ROI ROI1 in the reference image UI1 is at the same location as the first ROI ROI1 in the second ultrasound image UI2. The processor 140 performs motion estimation between the reference image UI1 and the second ultrasound image UI2 to estimate motion of the second ROI ROI2 in the reference image UI1. Since the motion estimation may be performed by using various known methods, a detailed description thereof is omitted here.

As shown in FIG. 6, the processor 140 sets the second ROI ROI2 on the second ultrasound image UI2 based on the estimated motion. The processor 140 compares the first ROI ROI1 in the second ultrasound image UI2 with the second ROI ROI2 therein and determines whether the second ROI ROI2 is inside the first ROI ROI1.

When the second ROI ROI2 in the second ultrasound image UI2 is inside the first ROI ROI1 therein, as shown in FIG. 6, the processor 140 determines that the second ultrasound image UI2 is not among the ultrasound images needed to form a panoramic image and controls the storage unit 130 not to store the second ultrasound image UI2 therein.

Figure 7:
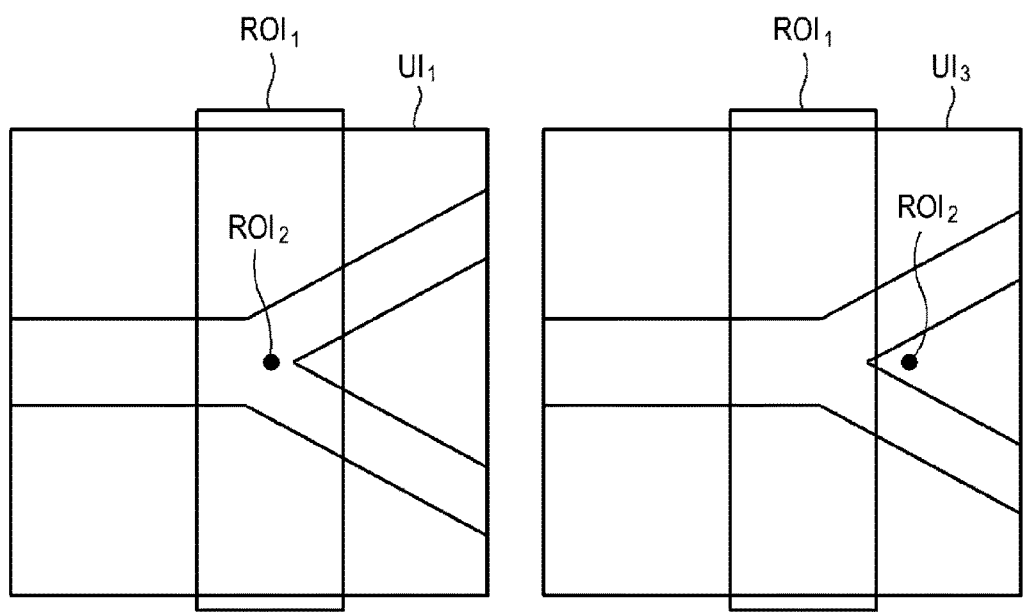

Referring to FIG. 7, the processor 140 then sets the first ROI ROI1 on a third ultrasound image UI3 based on input information (i.e., first input information). In this case, as described above, the first ROI ROI1 in the reference image UI1 is at the same location as the first ROI ROI1 in the third ultrasound image UI3.

The processor 140 performs motion estimation between the reference image UI1 and the third ultrasound image UI3 to estimate motion of the second ROI ROI2 in the reference image UI1. As shown in FIG. 7, the processor 140 sets the second ROI ROI2 on the third ultrasound image UI3 based on the estimated motion. The processor 140 compares the first ROI ROI1 in the third ultrasound image UI3 with the second ROI ROI2 therein and determines whether the second ROI ROI2 is inside the first ROI ROI1.

When the second ROI ROI2 in the third ultrasound image UI3 is not included in the first ROI ROI1 therein, as shown in FIG. 7, i.e., the second ROI ROI2 is outside of the first ROI ROI1, the processor 140 determines that the third ultrasound image UI3 is among the ultrasound images needed to form a panoramic image and controls the storage unit 130 to store third ultrasound image UI3 therein. Thus, the storage unit 130 stores the third ultrasound image UI3 according to a control of the processor 140.

Figure 8:
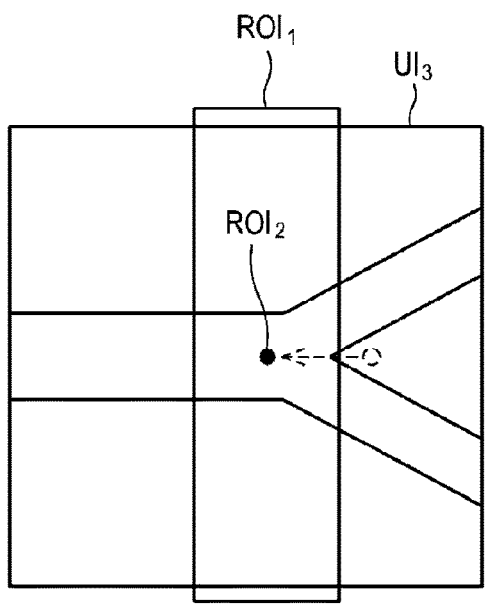
FIG. 8 is an exemplary diagram of movement of a second ROI to its original position, according to an exemplary embodiment of the present invention.

The processor 140 then sets the third ultrasound image UI3 as a new reference image and moves the second ROI ROI2 in the third ultrasound image UI3 to its original position, as shown in FIG. 8. More specifically, the processor 140 moves the second ROI ROI2 in the third ultrasound image UI3 to a location corresponding to the input information (i.e., information about the location of the second ROI ROI2). Thus, the second ROI ROI2 in the previous reference image UI1 is at the same location as the second ROI ROI2 in the third ultrasound image UI3 that is the new reference image.

The processor 140 performs the above-described processes on the remaining ultrasound images to extract ultrasound images needed to form a panoramic image.

Figure 9:
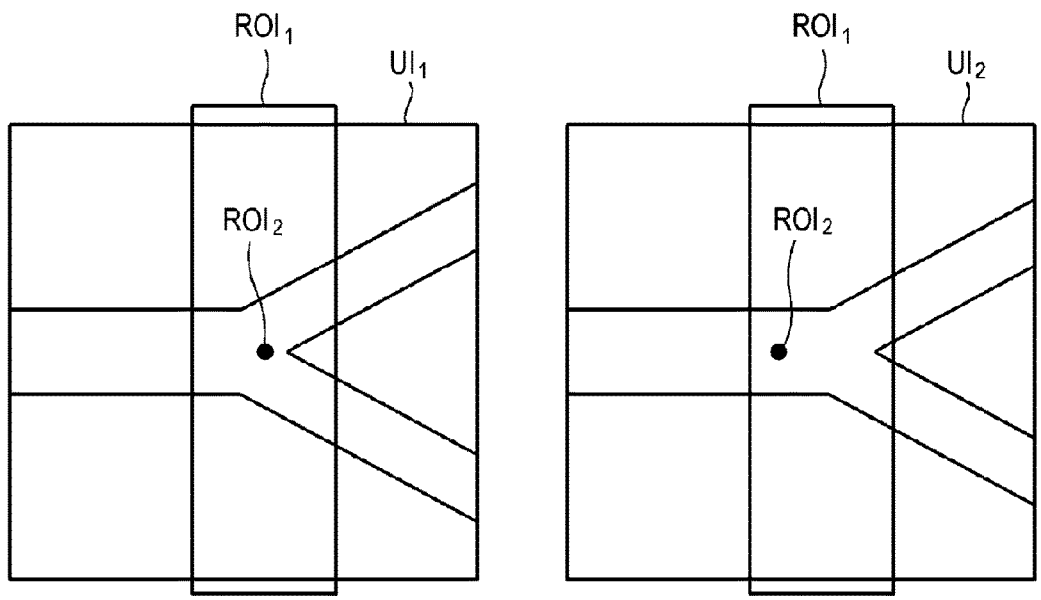
FIGS. 9 and 10 are exemplary diagrams showing setting of first and second ROIs on an ultrasound image, according to another exemplary embodiment of the present invention.

Referring to FIG. 9, in another embodiment, the processor 140 sets the second ROI ROI2 on the second ultrasound image UI2 based on input information (i.e., the first input information). In this case, the second ROI ROI2 in the reference image UI1 is at the same location as the second ROI ROI2 in the second ultrasound image UI2. The processor 140 performs motion estimation between the reference image UI1 and the second ultrasound image UI2 to estimate motion of the first ROI ROI1 in the reference image UI1.

As shown in FIG. 9, the processor 140 sets the first ROI ROI1 on the second ultrasound image UI2 based on the estimated motion. The processor 140 compares the first ROI ROI1 in the second ultrasound image UI2 with the second ROI ROI2 therein and determines whether the second ROI ROI2 is inside the first ROI ROI1. When the second ROI ROI2 in the second ultrasound image UI2 is inside the first ROI ROI1 therein, as shown in FIG. 9, the processor 140 determines that the second ultrasound image UI2 is not among the ultrasound images needed to form a panoramic image and controls the storage unit 130 not to store the second ultrasound image UI2 therein.

Figure 10:
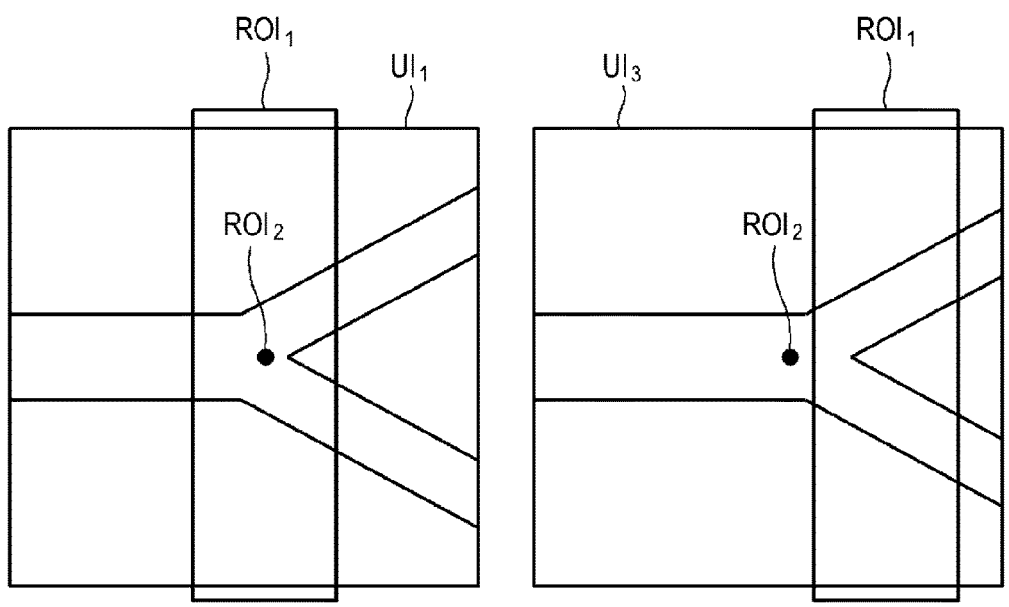

Referring to FIG. 10, subsequently, the processor 140 sets the second ROI ROI2 on the third ultrasound image UI3 based on input information (i.e., first input information). In this case, as described above, the second ROI ROI2 in the reference image UI1 is at the same location as the second ROI ROI2 in the third ultrasound image UI3.

The processor 140 performs motion estimation between the reference image UI1 and the third ultrasound image UI3 to estimate motion of the first ROI ROI1 in the reference image UI1. As shown in FIG. 10, the processor 140 sets the first ROI ROI1 on the third ultrasound image UI3 based on the estimated motion. The processor 140 compares the first ROI ROI1 in the third ultrasound image UI3 with the second ROI ROI2 therein and determines whether the second ROI ROI2 is inside the first ROI ROI1.

When the second ROI ROI2 in the third ultrasound image UI3 is not included in the first ROI ROI1 therein, as shown in FIG. 10, i.e., the first ROI ROI2 is outside of the second ROI ROI1, the processor 140 determines that the third ultrasound image UI3 is among the ultrasound images needed to form a panoramic image and controls the storage unit 130 to store the third ultrasound image UI3 therein.

Figure 11:
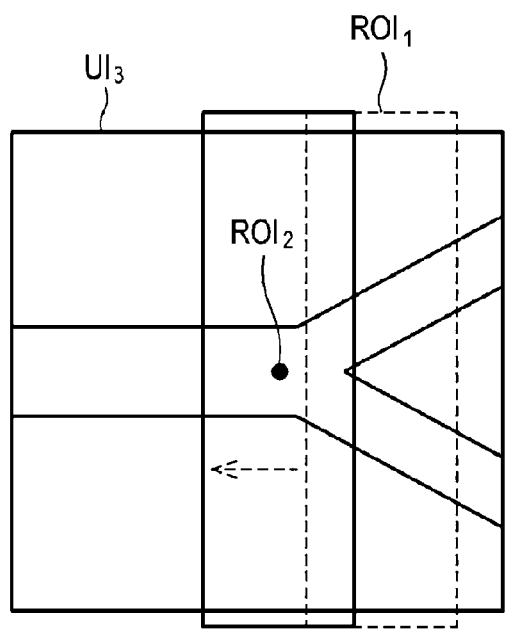
FIG. 11 is an exemplary diagram of movement of a first ROI to its original position, according to another exemplary embodiment of the present invention.

Then, the processor 140 sets the third ultrasound image UI3 as a new reference image and moves the first ROI ROI1 in the third ultrasound image UI3 to its original position, as shown in FIG. 11. More specifically, the processor 140 moves the first ROI ROI1 in the third ultrasound image UI3 to a location corresponding to the input information (i.e., information about the location of the first ROI ROI1). Thus, the first ROI ROI1 in the previous reference image UI1 is at the same location as the first ROI ROI1 in the third ultrasound image UI3 that is the new reference image.

The processor 140 performs the above-described processes on the remaining ultrasound images to extract ultrasound images needed to form a panoramic image.

Referring back to FIG. 3, the processor 140 extracts ultrasound images stored in the storage unit 130 and produces a panoramic image by using the extracted ultrasound images based on input information provided by the user input unit 120 (S312). Since the panoramic image may be created by using various known methods, a detailed description thereof is omitted here.

Referring back to FIG. 1, the ultrasound system 100 further includes the display unit 150. The display unit 150 displays ultrasound images generated by the processor 140. The display unit 150 also displays a panoramic image created by the processor 140.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An ultrasound system comprising:
   an ultrasound data acquisitor that includes an ultrasound probe and sequentially acquires ultrasound data corresponding to a living body;
   a processor that produces a plurality of ultrasound images by using the ultrasound data, sets a first ultrasound image as a reference image among the plurality of ultrasound images, sets a first region of interest (ROI) and a second ROI that is set within the first ROI on the reference image, performs motion estimation between the reference image and a second ultrasound image of the plurality of ultrasound images and between the reference image and a third ultrasound image of the plurality of ultrasound images to estimate motion of the first ROI or the second ROI, determines whether the second ROI in the second ultrasound image is outside the first ROI and whether the second ROI in the third ultrasound image is inside the first ROI, extracts the second ultrasound image as an ultrasound image needed for forming a panoramic image upon determination that the second ROI in the second ultrasound image is outside the first ROI therein, and excludes the third ultrasound image as an ultrasound image needed for forming the panoramic image upon determination that the second ROI in the second ultrasound image is within the first ROI therein; and a storage that stores the extracted second ultrasound image.

2. The system of claim 1, wherein the processor is further configured to set the first ROI on the second ultrasound image based on the first ROI in the reference image, perform motion estimation between the reference image and the second ultrasound image to estimate motion of the second ROI, and set the second ROI on the second ultrasound image based on the estimated motion.

3. The system of claim 2, wherein when the second ROI in the second ultrasound image is outside of the first ROI therein, the processor further moves the second ROI in the second ultrasound image to a position corresponding to the second ROI in the reference image and sets the second ultrasound image as the reference image.

4. The system of claim 1, wherein the processor is further configured to set the second ROI on the second ultrasound image based on the second ROI in the reference image, perform motion estimation between the reference image and the second ultrasound image to estimate motion of the first ROI, and set the first ROI on the second ultrasound image based on the estimated motion.

5. The system of claim 4, wherein when the second ROI in the second ultrasound image is outside of the first ROI therein, the processor further moves the first ROI in the second ultrasound image to a position corresponding to the first ROI in the reference image and sets the second ultrasound image as the reference image.

6. The system of claim 1, further comprising a user input unit configured to receive input information needed for setting the first ROI and the second ROI from a user.

7. The system of claim 1, wherein the processor is further configured to create the panoramic image at least based on the extracted second ultrasound image stored in the storage.

8. A method of providing a panoramic image, the method comprising:
sequentially acquiring ultrasound data corresponding to a living body;
producing a plurality of ultrasound images by using the ultrasound data;
setting a first ultrasound image as a reference image among the plurality of ultrasound images, setting a first region of interest (ROI) and a second ROI that is set within the first ROI on the reference image, performing motion estimation between the reference image and a second ultrasound image of the plurality of ultrasound images and between the reference image and a third ultrasound image of the plurality of ultrasound images to estimate motion of the first ROI or the second ROI, determining whether the second ROI in the second ultrasound image is outside the first ROI and whether the second ROI in the third ultrasound image is inside the first ROI, extracting the second ultrasound image as an ultrasound image needed for forming a panoramic image upon determination that the second ROI in the second ultrasound image is outside the first ROI therein, and excluding the third ultrasound image as an ultrasound image needed for forming the panoramic image upon determination that the second ROI in the second ultrasound image is within the first ROI therein; and storing the extracted second ultrasound image in a storage.

9. The method of claim 8, wherein the performing of motion estimation and the extracting the second ultrasound image comprise:
setting the first ROI on the second ultrasound image based on the first ROI in the reference image;
performing motion estimation between the reference image and the second ultrasound image to estimate motion of the second ROI; and
setting the second ROI on the second ultrasound image based on the estimated motion.

10. The method of claim 9, wherein the extracting the second ultrasound image further comprises moving the second ROI in the second ultrasound image to a position corresponding to the second ROI in the reference image and setting the second ultrasound image as the reference image.

11. The method of claim 8, wherein the performing motion estimation and the extracting the second ultrasound image comprise:
setting the second ROI on the second ultrasound image based on the second ROI in the reference image;
performing the motion estimation between the reference image and the second ultrasound image to estimate motion of the first ROI; and
setting the first ROI on the second ultrasound image based on the estimated motion.

12. The method of claim 11, wherein the extracting the second ultrasound image further comprises moving the first ROI in the second ultrasound image to a position corresponding to the first ROI in the reference image and setting the second ultrasound image as the reference image.

13. The method of claim 8, wherein the setting the first ROI and the second ROI, the performing motion estimation, and the extracting the second ultrasound image further comprise receiving input information needed for setting the first ROI and the second ROI from a user.

14. The method of claim 8, further comprising creating the panoramic image at least based on the extracted second ultrasound image stored in the storage.

* * * * *